(12) United States Patent
Filiberti

(10) Patent No.: US 11,673,004 B2
(45) Date of Patent: *Jun. 13, 2023

(54) X-RAY IMAGING SYSTEM WITH A COMBINED FILTER AND COLLIMATOR POSITIONING MECHANISM

(71) Applicant: SIEMENS HEALTHINEERS INTERNATIONAL AG, Palo Alto, CA (US)

(72) Inventor: Reto Filiberti, Baar (CH)

(73) Assignee: SIEMENS HEALTHINEERS INTERNATIONAL AG

( * ) Notice: Subject to any disclaimer, the term of this patent is extended or adjusted under 35 U.S.C. 154(b) by 0 days.

This patent is subject to a terminal disclaimer.

(21) Appl. No.: 17/665,596

(22) Filed: Feb. 7, 2022

(65) Prior Publication Data

US 2022/0161059 A1 May 26, 2022

Related U.S. Application Data

(63) Continuation of application No. 15/935,042, filed on Mar. 25, 2018, now Pat. No. 11,247,072.

(Continued)

(51) Int. Cl.
*A61N 5/10* (2006.01)
*H01H 13/02* (2006.01)
*H01H 9/16* (2006.01)
*H01H 13/70* (2006.01)
*A61B 6/00* (2006.01)
(Continued)

(52) U.S. Cl.
CPC ............ *A61N 5/1048* (2013.01); *A61B 6/461* (2013.01); *A61B 6/467* (2013.01); *H01H 9/161* (2013.01); *H01H 13/023* (2013.01); *H01H 13/70* (2013.01); *H05G 1/56* (2013.01); *H05G 1/58* (2013.01); *A61B 6/0487* (2020.08); *A61B 2017/00017* (2013.01); *A61B 2017/00199* (2013.01); *A61N 2005/1074* (2013.01); *H01H 2013/026* (2013.01); *H01H 2239/006* (2013.01); *H01H 2239/064* (2013.01); *H01H 2300/014* (2013.01); *H01H 2300/038* (2013.01); *H01H 2300/04* (2013.01); *H03K 17/18* (2013.01); *H03K 17/955* (2013.01); *H03K 17/96* (2013.01); *H03K 17/962* (2013.01)

(58) Field of Classification Search
None
See application file for complete search history.

(56) References Cited

U.S. PATENT DOCUMENTS

| 11,247,072 B2 * | 2/2022 | Filiberti ............... A61N 5/1048 |
| 2011/0013742 A1 | 1/2011 | Zaiki et al. |

(Continued)

*Primary Examiner* — David P Porta
*Assistant Examiner* — Mamadou Faye
(74) *Attorney, Agent, or Firm* — Su IP Consulting

(57) ABSTRACT

A radiation therapy system includes an X-ray imaging system that is configured with a combined and simplified filter and collimator positioning mechanism. In addition, an X-ray imager of the RT system is only positioned at a few discrete locations within a plane that is a fixed distance from the imaging X-ray source when generating X-ray images. As a result, for each of these discrete imaging positions, the simplified filter and collimator positioning mechanism positions a specific collimator-filter combination in a specific location between the X-ray source and the imager.

20 Claims, 9 Drawing Sheets

Related U.S. Application Data

(60) Provisional application No. 62/566,301, filed on Sep. 29, 2017.

(51) Int. Cl.
| | | |
|---|---|---|
| *H05G 1/58* | (2006.01) | |
| *H05G 1/56* | (2006.01) | |
| *A61B 17/00* | (2006.01) | |
| *H03K 17/18* | (2006.01) | |
| *H03K 17/96* | (2006.01) | |
| *A61B 6/04* | (2006.01) | |
| *H03K 17/955* | (2006.01) | |

(56) References Cited

U.S. PATENT DOCUMENTS

| | | |
|---|---|---|
| 2012/0314841 A1 | 12/2012 | Heid |
| 2013/0221243 A1 | 8/2013 | Perkins |
| 2016/0135779 A1 | 5/2016 | Kim et al. |
| 2017/0065233 A1 | 3/2017 | Yang |
| 2019/0099622 A1 | 4/2019 | Filiberti |

\* cited by examiner

X-RAY IMAGING SYSTEM WITH A COMBINED FILTER AND COLLIMATOR POSITIONING MECHANISM

CROSS-REFERENCE TO RELATED APPLICATIONS

The present application is a continuation under 35 U.S.C. § 120 of U.S. patent application Ser. No. 15/935,042, filed Mar. 25, 2018, which claims the benefit of U.S. Provisional Application No. 62/566,301, filed Sep. 29, 2017. The aforementioned U.S. Patent Application and U.S. Provisional Application, including any appendices or attachments thereof, are hereby incorporated by reference in their entirety.

BACKGROUND

Unless otherwise indicated herein, the approaches described in this section are not prior art to the claims in this application and are not admitted to be prior art by inclusion in this section.

Radiation therapy, which is the use of ionizing radiation, is a localized treatment for a specific target tissue, such as a cancerous tumor. Ideally, radiation therapy is performed on target tissue (also referred to as the planning target volume) that spares the surrounding normal tissue from receiving doses above specified tolerances, thereby minimizing risk of damage to healthy tissue. Prior to the delivery of radiation therapy, an imaging system is typically employed to provide a three dimensional image of the target tissue and surrounding area. From such imaging, the size and mass of the target tissue can be estimated and an appropriate treatment plan generated and target volume determined.

So that the prescribed dose is correctly supplied to the planning target volume during radiation therapy, the patient should be correctly positioned relative to the linear accelerator that provides the radiation therapy. Typically, patient geometric data is checked before and during the treatment, to ensure correct patient placement. This process is referred to as image guided radiation therapy (IGRT), and involves the use of an imaging system to view target tissues while radiation treatment is delivered to the planning target volume. IGRT incorporates imaging coordinates from the treatment plan to ensure the patient is properly aligned for treatment in the radiation therapy device.

One challenge of radiation therapy is generating sufficiently clear images of the planning target volume using the lowest possible imaging dose. To that end, RT systems commonly include shaped filters, referred to as "bow-tie" filters, which are in the path of an imaging beam and maintain a more uniform distribution of X-ray photons across the field of view. Furthermore, to limit the size and shape of an imaging beam, and to limit X-ray scatter that can degrade image quality, a collimator is also typically positioned in the path of the imaging beam. However, correctly positioning a bow-tie filter and a collimator in an RT system can be a complex problem. This is because, for a given position of the imager, both the collimator and bow-tie filter must be precisely and independently positioned relative to the imager and to each other in order to properly shape the imaging beam. Further, to maximize flexibility in image acquisition positions, RT systems typically include an imager for receiving imaging X-rays that can be positioned with multiple degrees of freedom about a patient. Thus, such RT systems include a complex imaging collimation system with multiple (typically four) completely independent collimator blades for shaping the imaging beam. Adding further mechanical and control complexity, such RT system generally also includes an independent movement system for positioning the bow-tie filter.

In light of the above, there is a need in the art for radiation therapy systems that address the above-described challenges.

BRIEF DESCRIPTION OF THE DRAWINGS

Features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
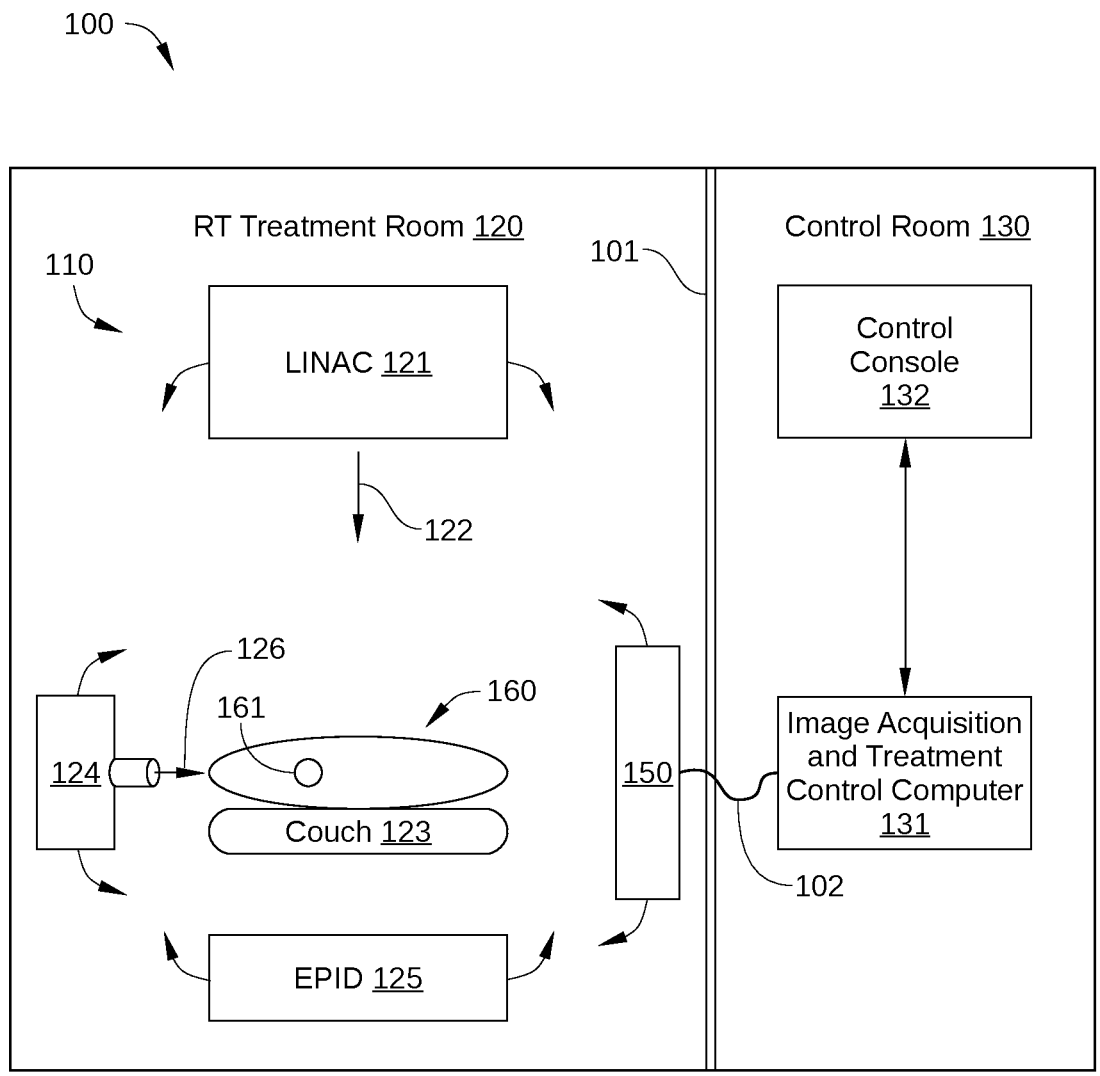
FIG. 1 illustrates a clinical environment in which an embodiment of the present disclosure can be integrated.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

As noted above, when radiation treatment (RT) treatment is applied accurately to targeted tissue in a patient, there is minimal impact on healthy tissue surrounding the targeted tissue. However, the positioning of the collimator and filter for the imaging system included in RT systems is necessarily complex, including a movement system for multiple independently positioned collimator blades (to adjust the imaging field) and another movement system for an independently positioned bow-tie filter (to provide a field of view that receives a uniform distribution of X-ray photons). According to various embodiments, an RT system includes an X-ray imaging system that is configured with a combined and simplified filter and collimator positioning mechanism. In addition, in some embodiments, an X-ray imager of the RT system is only positioned at a few discrete locations within a plane that is a fixed distance from the imaging X-ray source when generating X-ray images. As a result, for each of these discrete imaging positions, the positioning mechanism positions a specific collimator-filter combination in a specific location between the X-ray source and the imager. That is, for each of the discrete locations at which the imager is positioned for generating images, the positioning mechanism implements a single corresponding collimator-filter configuration. Thus, the complex systems usually employed for precisely changing the position the collimator and the filter in real time are not needed.

FIG. 1 illustrates a clinical environment 100 in which an embodiment of the present disclosure can be integrated. Clinical environment 100 includes a radiotherapy (RT) treatment room 120 with an RT treatment system 110 disposed therein and a control room 130, separated by a shielded wall 101. RT treatment system 110 includes a linear accelerator (LINAC) 121 that generates a megavolt (MV) treatment beam 122 of high energy X-rays (or in some embodiments electrons), a patient table or couch 123, a kilovolt (kV) X-ray source 124, an X-ray imager 150, and, in some embodiments, an MV electronic portal imaging device (EPID) 125. Control room 130 includes an image acquisition and treatment control computer 131 communicatively coupled to X-ray imager 150 via an acquisition cable 102, and an associated control console 132.

Also shown in FIG. 1 is a patient 160, positioned on couch 123 for RT treatment. Patient 160 includes a target region 161. Target region 161 may be, for example, a tumor to receive RT treatment, and can be located in different regions of the body of patient 160, such as the head, thorax, or leg. Different regions of the human body each have a different cross-sectional profile. For example, the head is generally round in cross-section whereas the torso is typically thicker laterally than vertically. Consequently, to create a more uniform imaging beam intensity across the surface of X-ray imager 150, a different compensating filter is typically employed during imaging, depending on the region of the body being imaged. The correct compensating filter can appropriately reduce the imaging beam intensity at the periphery of the beam. Thus, the imaging system included in RT treatment system 110 typically includes two or more compensating filters (not shown in FIG. 1), which are described in greater detail below in conjunction with FIGS. 5 and 6.

LINAC 121 customizes a treatment beam 122 to conform to the shape of a tumor in target region 161 of patient 160. Thus, LINAC 121 destroys cancer cells while sparing surrounding normal tissue when the location of target region 161 is precisely known. KV X-ray source 124 is an X-ray source for generating an imaging beam 126, which is directed toward X-ray imager 150 for imaging target region 161 and surrounding areas during RT treatment. For example, in some embodiments, clinical environment 100 is employed for image-guided radiation therapy (IGRT), which uses image guidance procedures for target localization before and during treatment. In such embodiments, the images used to precisely monitor the current location of target region 161 are generated with kV X-ray source 124 and X-ray imager 150. Alternatively or additionally, in some embodiments, images generated with kV X-ray source 124 and X-ray imager 150 can be employed in intensity-modulated radiation therapy (IMRT) applications. In either IGRT or IMRT applications, elements of RT treatment system 110 rotate about couch 123 during RT treatment. For example, in some embodiments, LINAC 121, EPID 125, kV X-ray source 124, and X-ray imager 150 rotate about couch 123 as indicated. One embodiment of RT treatment system 110 is described below in conjunction with FIG. 2.

Figure 2:
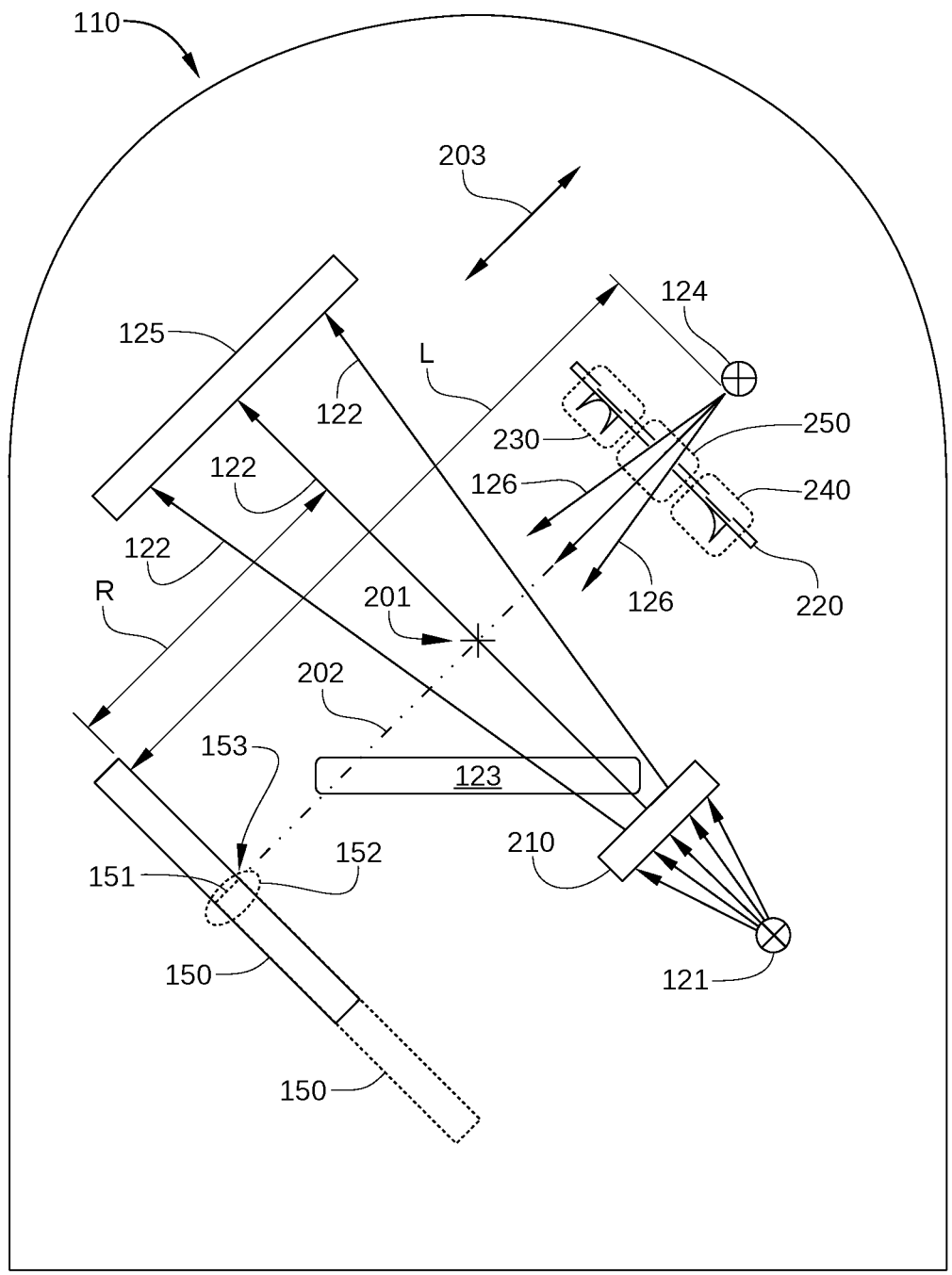
FIG. 2 schematically illustrates a front view of an RT treatment system, according to various embodiments of the present disclosure.

FIG. 2 schematically illustrates a front view of RT treatment system 110, according to various embodiments of the present disclosure. In FIG. 2, elements of RT treatment system 110 (LINAC 121, EPID 125, a treatment beam collimator 210, kV X-ray source 124, and X-ray imager 150) are shown partially rotated about couch 123 at a specific point in time during operation. In the embodiment illustrated in FIG. 2, kV X-ray source 124 and X-ray imager 150 are shown at a 45° rotation position while LINAC 121 and EPID 125 are shown in FIG. 2 at the corresponding 135° rotation position.

LINAC 121 (which generates treatment beam 122), EPID 125, a treatment beam collimator 210, kV X-ray source 124, and X-ray imager 150 rotate about a center point of rotation 201, which is disposed along an X-ray path 202 from kV X-ray source 124 to a point on an X-ray detection surface (not shown) of X-ray imager 150. For example, in some embodiments, X-ray path 202 is a shortest path from kV X-ray source 124 to a point on an X-ray detection surface (not shown) of X-ray imager 150. Generally, X-ray path 202 has a length L and is the path from kV X-ray source 124 to a center point of X-ray imager 150 when X-ray imager 150 is located at a center imaging position, thereby defining a vertical direction 203 between kV X-ray source 124 and X-ray imager 150. In a center imaging position, which is shown in FIG. 2, X-ray imager 150 is substantially centered on X-ray path 202. By contrast, in a lateral offset position (indicated by dashed lines), an edge 151 and/or an edge portion 152 of X-ray imager 150 is a distance along X-ray path 202 from kV X-ray source 124 that is equal to length L. In either the center imaging position or the lateral offset position, at least a portion of X-ray imager 150 is a fixed rotational distance R along X-ray path 202 from center point of rotation 201. In some embodiments, RT treatment system 110 is configured to generate X-ray images with X-ray imager 150 in at least the center imaging position and the lateral offset position, as appropriate for a particular imaging application. Examples of the positioning of X-ray imager 150 for various imaging applications are illustrated in FIGS. 3A, 3B, and 3C.

Figure 3C:
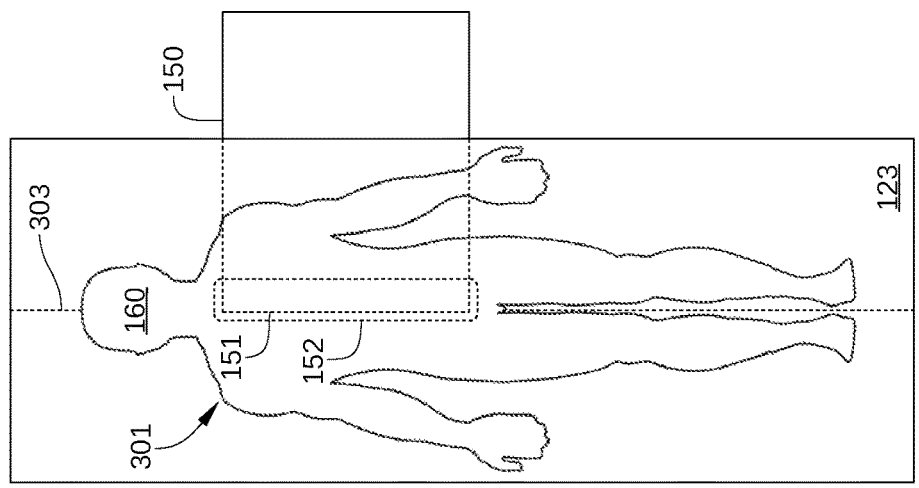
FIGS. 3A, 3B, and 3C schematically illustrate an X-ray imager when positioned for generating images in a center imaging position and in a lateral offset position, according to various embodiments of the present disclosure.
Figure 3B:
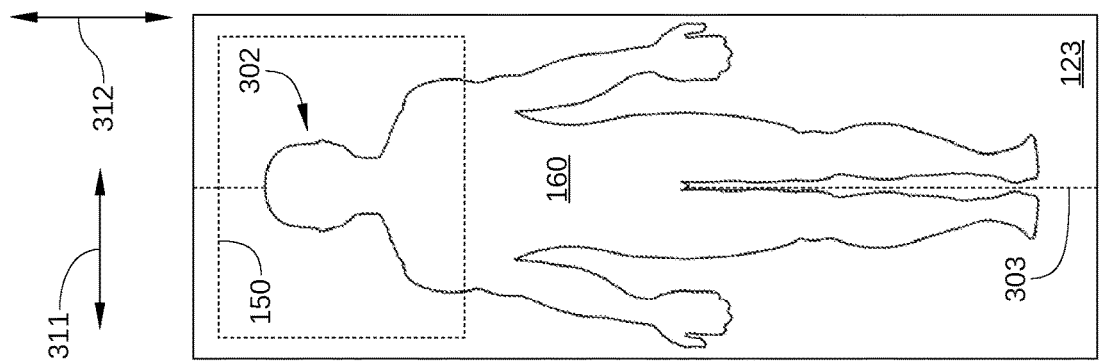
Figure 3A:
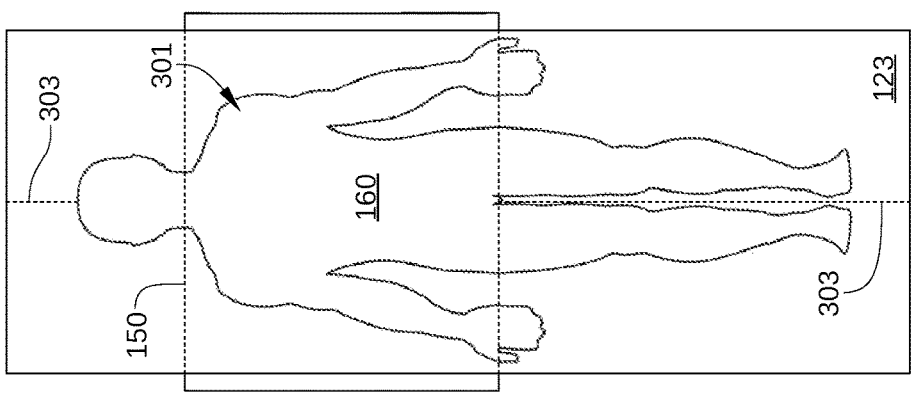

FIGS. 3A, 3B, and 3C schematically illustrate X-ray imager 150 when positioned for generating images in a center imaging position and in a lateral offset position, according to various embodiments of the present disclosure. Specifically, FIG. 3A illustrates a view of X-ray imager 150 from kV X-ray source 124 when X-ray imager 150 and couch 123 are positioned for generating X-ray images of the thorax 301 of patient 160. FIG. 3B illustrates a view of X-ray imager 150 from kV X-ray source 124 when X-ray imager 150 and couch 123 are positioned for generating X-ray images of the head 302 of patient 160. FIG. 3C illustrates a view of X-ray imager 150 from kV X-ray source 124 when X-ray imager 150 and couch 123 are positioned for generating X-ray images of thorax 301 of patient 160 in half-fan cone-beam computed tomography (CBCT) mode. In many applications, X-ray imager 150 and kV X-ray source 124 (not shown in FIGS. 3A, 3B, and 3C) rotate about couch 123. Therefore, in such applications, X-ray imager 150 and kV X-ray source 124 are not fixed in position relative to couch 123. Thus, for reference, couch 123 and X-ray imager 150 are shown in FIGS. 3A, 3B, and 3C at a point in time when kV X-ray source 124 has rotated to a position directly above couch 123 and X-ray imager 150 is rotated to a position below couch 123. That is, kV X-ray source 124 and X-ray imager 150 are shown in FIGS. 3A, 3B, and 3C at a 0° rotation position.

In FIG. 3A, X-ray imager 150 is positioned in a center imaging position to enable X-ray imaging of thorax 301 of patient 160. Therefore, when kV X-ray source 124 is rotated to a position directly above couch 123, X-ray imager 150 is positioned directly below couch 123 and is centered in lateral direction 311 on a longitudinal axis 303 of couch 123. That is, a center point 153 of an X-ray detection surface of X-ray imager 150 is disposed on or proximate X-ray path 202. It is noted that in some embodiments, X-ray imager 150 and couch 123 are positioned in the center imaging position as shown for generating either planar images, live-imaging, or full-fan CBCT images of thorax 301 of patient 160.

In FIG. 3B, X-ray imager 150 is positioned in a center imaging position to enable X-ray imaging of head 302 of patient 160. Therefore, when kV X-ray source 124 is rotated to a position directly above couch 123, X-ray imager 150 is positioned directly below couch 123 and is centered in lateral direction 311 on longitudinal axis 303 of couch 123. To direct imaging beam 126 (not shown in FIG. 3B) to head 302, couch 123 is translated in a longitudinal direction 312 relative to X-ray imager 150. It is noted that in some embodiments, X-ray imager 150 and couch 123 are positioned in the center imaging position shown in FIG. 3B for generating either planar images or full-fan CBCT images of head 302 of patient 160. In embodiments in which full-fan CBCT image of head 302 are generated, a specific shaping filter (not shown) is typically employed to generate a more uniform intensity of imaging beam 126 across X-ray imager 150, as described in greater detail below. By contrast, in embodiments in which planar (2D) images and/or live images are generated, a shaping filter is generally not employed.

In FIG. 3C, X-ray imager 150 is positioned in a lateral offset position to enable half-fan CBCT X-ray imaging of thorax 301 of patient 160. In half-fan CBCT X-ray imaging, only half of thorax 302 is irradiated with imaging beam 126 (not shown in FIG. 3C) for each projection generated as part of the volumetric data set for the CBCT imaging process. Therefore, when kV X-ray source 124 is rotated to a position directly above couch 123, X-ray imager 150 is positioned to be displaced from the center imaging position in lateral direction 311, which is a direction perpendicular to X-ray path 202 (shown in FIG. 2). In some embodiments, when X-ray imager 150 is in the lateral offset position, X-ray imager 150 is positioned so that edge 151 of X-ray imager 150 is substantially aligned with longitudinal axis 303. Alternatively, in some embodiments, when X-ray imager 150 is in the lateral offset position, X-ray imager 150 is positioned so that edge portion 152 of X-ray imager 150 is substantially aligned with longitudinal axis 303. It is noted that in some embodiments, X-ray imager 150 and couch 123 are positioned in the lateral offset imaging position shown in FIG. 3C for generating half-fan CBCT images of thorax 301 of patient 160. In such embodiments, a specific compensating filter (not shown) is typically employed to generate a more uniform intensity of imaging beam 126 across X-ray imager 150, as described in greater detail below. The compensating filter employed in the lateral offset position is generally a different filter than the compensating filter employed in the center imaging position.

Returning to FIG. 2, RT treatment system 110 also includes a positioning mechanism 220, a first combined filter-collimator assembly 230, a second combined filter-collimator assembly 240, and a filter-free collimator 250. According to various embodiments of the present disclosure, positioning mechanism 220 is disposed between kV X-ray source 124 and X-ray imager 150, and is configured to selectively position one of first combined filter-collimator assembly 230, second combined filter-collimator assembly 240, or filter-free collimator 250 along X-ray path 202. Thus, when X-ray imager 150 is in the center imaging position for generating planar X-ray images of patient 160, positioning mechanism 220 can be employed to position filter-free collimator 250 along X-ray path 202; when X-ray imager 150 is in the center imaging position for generating full-fan CBCT images of patient 160, positioning mechanism 220 can be employed to position first combined filter-collimator assembly 230 along X-ray path 202; and when X-ray imager 150 is in the lateral offset imaging position for generating half-fan CBCT images of patient 160, positioning mechanism 220 can be employed to position second combined filter-collimator assembly 240 along X-ray path 202.

Positioning mechanism 220 can include any suitable mechanism operable to selectively position one of first combined filter-collimator assembly 230, second combined filter-collimator assembly 240, or filter-free collimator 250 along X-ray path 202. For example, in some embodiments, positioning mechanism 220 includes a slider mechanism that is motorized and has a simple 2-channel position detection system, such as a stepper motor. Various embodiments of positioning mechanism 220 are described in greater detail below in conjunction with FIGS. 7 and 8.

Generally, RT treatment system 110 includes multiple combined filter-collimator assemblies. Each such combined filter-collimator assembly includes a different compensating filter, and each compensating filter is configured to generate uniform imaging beam intensity 126 across X-ray imager 150 for a different imaging position and/or application of X-ray imager 150. Thus, in the embodiment illustrated in FIG. 2, RT treatment system 110 includes two combined filter-collimator assemblies—one for each imaging position of X-ray imager 150. In other embodiments, RT treatment system 110 includes more than two or only a single combined filter-collimator assembly. In such embodiments, each combined filter-collimator assembly is configured to suitably modify imaging beam 126 for a different imaging position of X-ray imager 150 relative to X-ray path 202, and typically includes a compensating filter that is unique from other compensating filters included in the other combined filter-collimator assemblies of RT treatment system 110.

X-ray imager 150 generates images from a small number of discrete locations, two possible examples of which are illustrated in FIG. 2. According to various embodiments of the present disclosure, these discrete imaging locations for X-ray imager 150 vary in a single direction relative to kV X-ray source 124. Specifically, the discrete imaging locations for X-ray imager 150 are disposed in a plane that is perpendicular to X-ray path 202. For example, in the embodiment illustrated in FIG. 2, X-ray imager 150 is fixed relative to kV X-ray source 124 longitudinally, i.e., in longitudinal direction 312 shown in FIG. 3, which is the direction directly out of the page in FIG. 2. Thus, at each imaging position, X-ray imager 150 is disposed in a plane that includes kV X-ray source 124 and each of the other imaging positions of X-ray imager 150. In addition, in the embodiment illustrated in FIG. 2, X-ray imager 150 is fixed relative to kV X-ray source 124 in vertical direction 203, i.e., in the direction parallel to X-ray path 202. Thus, at each imaging position, a portion of X-ray imager 150 is disposed along X-ray path at a distance L from kV X-ray source 124.

In sum, RT treatment system 110 includes a simplified imaging system that can be used for the most common treatments and imaging positions, but not for all possible treatments. For treatment cases that rely on the imaging positions for which RT treatment system 110 is configured, RT treatment system 110 can employ state-of-the-art technology, including IMRT, IGRT, and the like, but without the drawbacks inherent in more complex systems. Specifically, in place of reduced flexibility, RT system 110 includes vertically and laterally fixed imager positions (described above), and a simplified kV collimation system. For example, the most common uses of the collimation/filter system for RT imaging systems employ the collimator in the center imaging position and the lateral offset (half-fan CBCT) imaging position. Thus, having X-ray imager 150 fixed in vertical direction 203 and longitudinal direction 312 does not affect imaging, but greatly simplifies the kV collimation/filter system. Having no adjustability in the longitudinal field size allows for fixed collimation in that direction. For each imaging position in the lateral direction, a suitable fixed compensating filter can be implemented with positioning mechanism 220 as appropriate, such as a bow-tie filter. Examples of various imaging positions and the positioning of suitable compensating filters and lateral collimation via positioning mechanism 220 are described below in conjunction with FIGS. 4-6.

Figure 4:
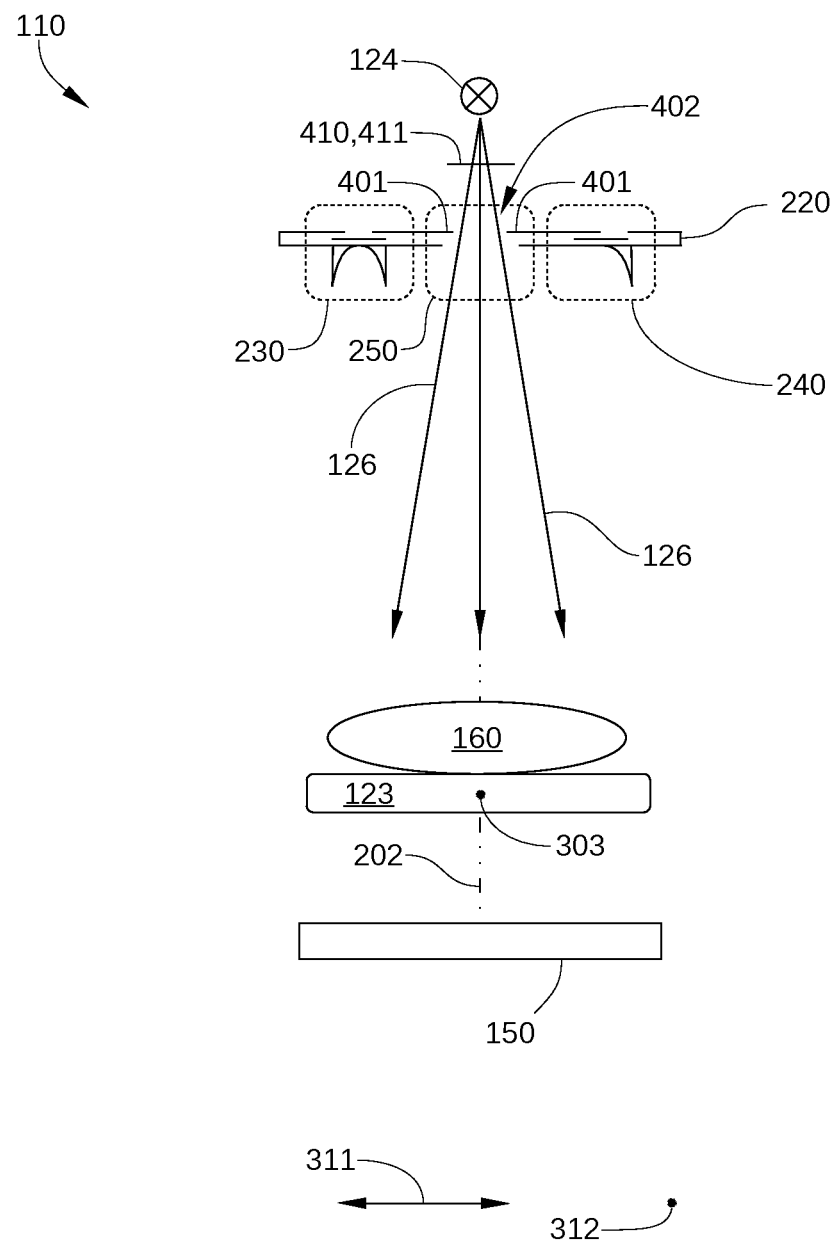
FIG. 4 schematically illustrates components of RT treatment system configured to generate planar images and/or live-images of a patient, according to an embodiment of the present disclosure.

FIG. 4 schematically illustrates components of RT treatment system 110 configured to generate planar images and/or live-images of patient 160, according to an embodiment of the present disclosure. Specifically, X-ray imager 150 and couch 123 are in the center imaging position illustrated in FIG. 3A, and positioning mechanism 220 has selectively positioned filter-free collimator 250 along X-ray path 202. Thus, kV X-ray source 124 is rotated to a position directly above couch 123, and X-ray imager 150 is positioned directly below couch 123 and is centered in lateral direction 311 on X-ray path 202 and on longitudinal axis 303 of couch 123. Since X-ray imager 150 is used to generate planar images and/or live-images of patient 160 in the embodiment illustrated in FIG. 4, kV X-ray source 124 and X-ray imager 150 are generally static relative to patient 160 at any selected rotation angle around the rotation center 201.

Filter-free collimator 250 is configured to limit the extent of X-ray exposure in lateral direction 311 of patient 160 and of X-ray imager 150. For example, in some embodiments, filter-free collimator 250 includes two blades 401 with an opening 402 therebetween that is sized to enable imaging beam 126 to reach most or all of the detector surface of X-ray imager 150 as shown. In some embodiments, blades 401 each include a plate of lead, tungsten, or any other suitable material for absorbing incident X-rays. Generally, opening 402 is fixed.

In some embodiments, RT treatment system 110 further includes a longitudinal collimator 410 that limits the extent of X-ray exposure in longitudinal direction 312, which in FIG. 4 is directly out of the page. In such embodiments, longitudinal collimator 410 can include two blades 411 with an opening (not visible in FIG. 4) therebetween that is sized to enable imaging beam 126 to reach most or all of the detector surface of X-ray imager 150 in longitudinal direction 312 (which is out of page in FIG. 4). Thus, together longitudinal collimator 410 and filter-free collimator 250 define the rectangular region of X-ray imager 150 and patient 160 that is exposed to imaging beam 126. Blades 411 can each include a plate formed from similar materials as described above for blades 401.

Figure 5:
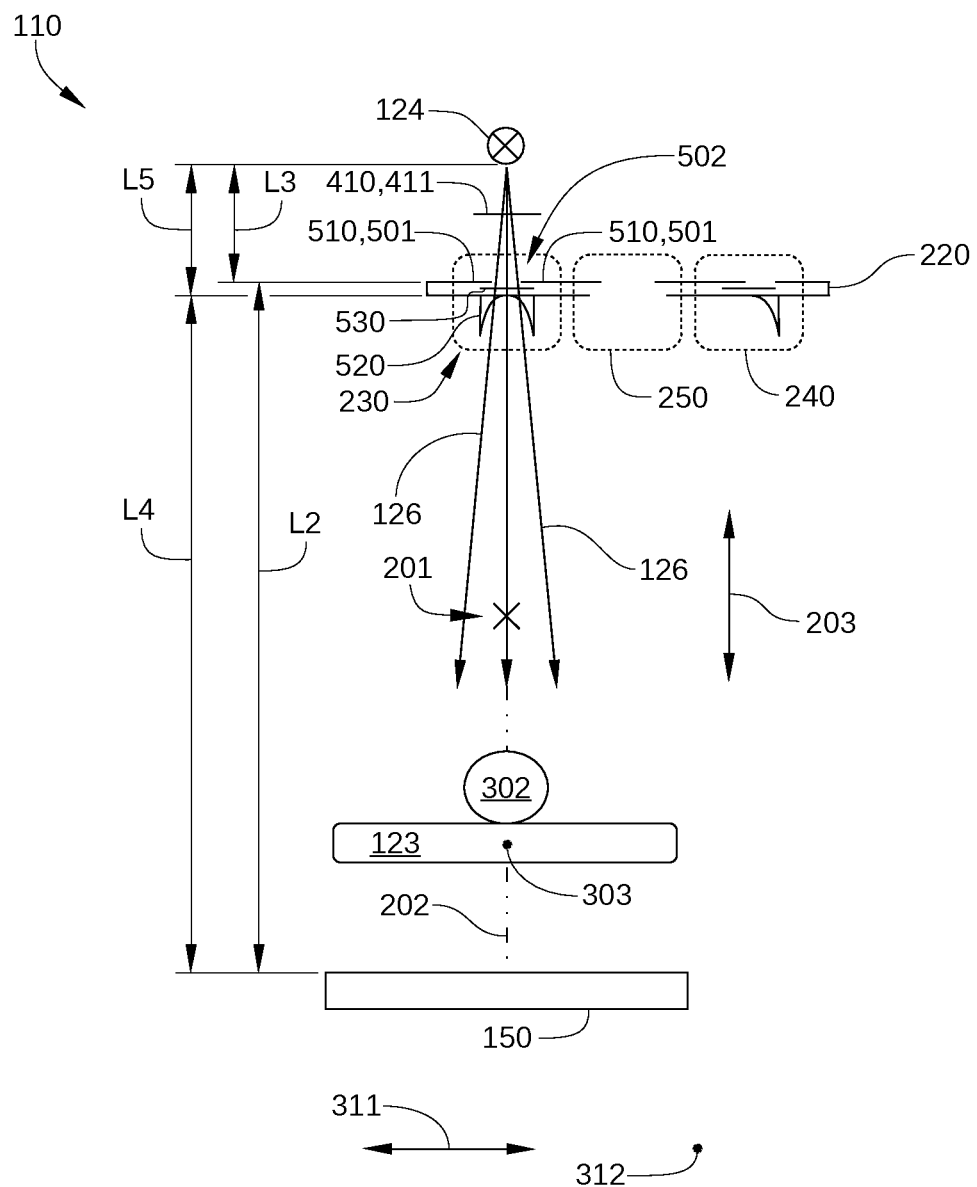
FIG. 5 schematically illustrates components of an RT treatment system configured to enable CBCT imaging of a head or other localized portion of a patient, according to an embodiment of the present disclosure.

FIG. 5 schematically illustrates components of RT treatment system 110 configured to enable CBCT imaging of head 302 or other localized portion of patient 160, according to an embodiment of the present disclosure. Specifically, X-ray imager 150 and couch 123 are in the center imaging position illustrated in FIG. 3B, and positioning mechanism 220 has selectively positioned first combined filter-collimator assembly 230 along X-ray path 202. Typically, positioning mechanism 220 positions first combined filter-collimator assembly 230 in X-ray path 202 between longitudinal collimator 410 and X-ray imager 150.

KV X-ray source 124 and X-ray imager 150 rotate about center point of rotation 201 and are therefore not fixed in position relative to couch 123. FIG. 5 depicts RT treatment system 110 when kV X-ray source 124 is rotated to a position directly above couch 123 and X-ray imager 150 is positioned directly below couch 123. As shown, at such a point in time, X-ray imager 150 is centered in lateral direction 311 on X-ray path 202 and on longitudinal axis 303 of couch 123.

First combined filter-collimator assembly 230 includes a collimator 510, a compensating filter 520, and, in some embodiments, an intensity filter 530. Collimator 510 is configured to limit the extent of X-ray exposure in lateral direction 311 of patient 160 and to align incident imaging beam 126 with X-ray imager 150. For example, in some embodiments, collimator 510 includes two blades 501 with an opening 502 therebetween that is sized to enable imaging beam 126 to reach most or all of the detector surface of X-ray imager 150 as shown. Blades 501 can each include a plate formed from similar materials as described above for blades 401. Generally, opening 502 is fixed. Compensating filter 520 is configured to create a more uniform intensity of imaging beam 126 across the surface of X-ray imager 150 when X-ray imager 150 is in the center imaging position. Compensating filter 520 can be, for example, a bowtie filter, and in some embodiments, can be formed from aluminum.

Intensity filter 530 is configured to provide additional X-ray filtering, and is typically a uniform plate of X-ray absorbing material, such as titanium. In some embodiments, intensity filter 530 is physically coupled to or mounted on first combined filter-collimator assembly 230, and therefore is moved together with first combined filter-collimator assembly 230 by positioning mechanism 220. Alternatively, intensity filter 530 can be moved into position in X-ray path 202 separately from first combined filter-collimator assembly 230. Similarly, in some embodiments, collimator 510 is physically coupled to or mounted on compensating filter 520, and therefore is moved together with compensating filter 520 as a single assembly by positioning mechanism 220. Alternatively, collimator 510 can be moved into position in X-ray path 202 separately from compensating filter 520. Together, longitudinal collimator 410 and collimator 510 define the rectangular region of X-ray imager 150 and patient 160 that is exposed to imaging beam 126.

As noted above, during operation X-ray imager 150 is fixed in vertical direction 203 relative to kV X-ray source 124. As a result, from a fixed location in vertical direction 203 relative to kV X-ray source 124 and X-ray imager 150, collimator 510 correctly limits the extent of imaging beam 126 in lateral direction 311. That is, real-time variation of the position of collimator 510 in vertical direction 203 is not necessary. Similarly, from a fixed location in vertical direction 203 relative to kV X-ray source 124 and X-ray imager 150, compensating filter 520 can correctly equalize or balance the intensity of imaging beam 126 that reaches X-ray imager 150, and real-time variation of the position of compensating filter 520 in vertical direction 203 is not necessary. Thus, X-ray imager 150 can generate state-of-the-art X-ray images and volumetric data sets without the complex positioning mechanism employed in conventional RT systems. For example, in the embodiment illustrated in FIG. 5, collimator 510 is positioned a fixed vertical distance L2 from X-ray imager 150 and a fixed vertical distance L3 from kV X-ray source 124. That is, during imaging, vertical distance L2 (between collimator 510 and X-ray imager 150) and vertical distance L3 (between collimator 510 and kV X-ray source 124) each remain constant. Similarly, compensating filter 520 is positioned a fixed vertical distance L4 from X-ray imager 150 and a fixed vertical distance L5 from kV X-ray source 124. Consequently, during imaging, vertical distance L4 (between compensating filter 520 and X-ray imager 150) and vertical distance L5 (between compensating filter 520 and kV X-ray source 124) each remain constant.

It is noted that for each other imaging position of X-ray imager 150, positioning mechanism 220 is configured to position a different combined filter-collimator assembly in X-ray path 202. Second combined filter-collimator assembly 240 is just one such example. Each different combined filter-collimator assembly includes a different configuration of compensating filter than compensating filter 520 and a different collimator than collimator 510. Also, in each different combined filter-collimator assembly, the vertical distances between the compensating filter, collimator, X-ray imager 150, and kV X-ray source 124 can be different than vertical distances L2, L3, L4, and L5.

Figure 6:
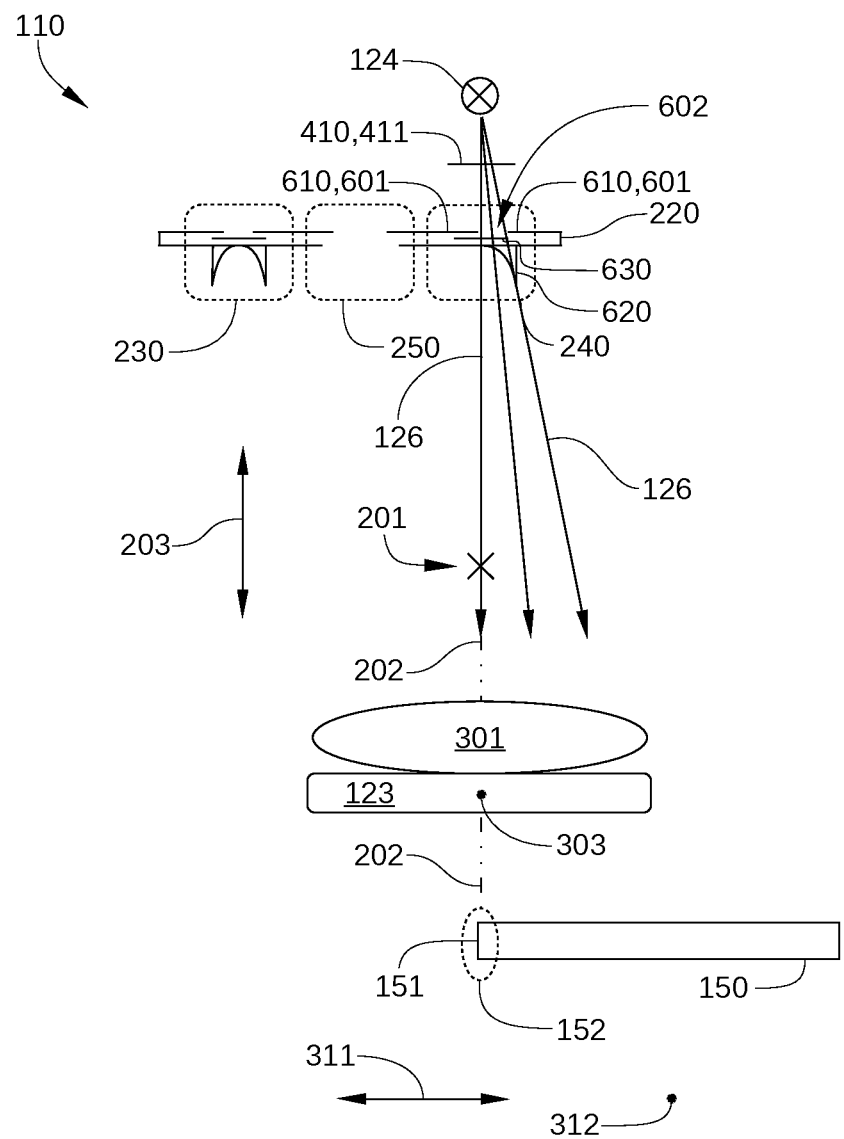
FIG. 6 schematically illustrates components of an RT treatment system configured to enable half-fan CBCT imaging of a thorax or other large region of a patient, according to an embodiment of the present disclosure.

FIG. 6 schematically illustrates components of RT treatment system 110 configured to enable half-fan CBCT imaging of thorax 301 or other large region of patient 160, according to an embodiment of the present disclosure. Specifically, X-ray imager 150 is in the lateral offset imaging position illustrated in FIG. 3C, and positioning mechanism 220 has selectively positioned second combined filter-collimator assembly 240 along X-ray path 202. Typically, positioning mechanism 220 positions second combined filter-collimator assembly 240 in X-ray path 202 between longitudinal collimator 410 and X-ray imager 150.

In FIG. 6, KV X-ray source 124 and X-ray imager 150 rotate about center point of rotation 201 and are therefore not fixed in position relative to couch 123. FIG. 6 depicts RT treatment system 110 when kV X-ray source 124 is rotated to a position directly above couch 123 and X-ray imager 150 is positioned below couch 123. As shown, at such a point in time, X-ray imager 150 is in the lateral offset imaging position to enable half-fan CBCT X-ray imaging of thorax 301 of patient 160. Thus, X-ray imager 150 is positioned so that edge 151 and/or edge portion 152 of X-ray imager 150 is substantially aligned with longitudinal axis 303 of couch 123.

Second combined filter-collimator assembly 240 includes a collimator 610, a compensating filter 620, and, in some embodiments, an intensity filter 630. Collimator 610 is configured to limit the extent of X-ray exposure in lateral direction 311 of patient 160 and to align incident imaging beam 126 with X-ray imager 150. For example, in some embodiments, collimator 610 includes two blades 601 with an opening 602 therebetween that is sized to enable imaging beam 126 to reach most or all of the detector surface of X-ray imager 150 as shown. Blades 601 can each include a plate formed from similar materials as described above for blades 401. Generally, opening 602 is fixed. Compensating filter 620 is configured to create a more uniform intensity of imaging beam 126 across the surface of X-ray imager 150 when X-ray imager 150 is in the lateral offset imaging position. Compensating filter 620 can be, for example, a half-bowtie filter, and in some embodiments, can be formed from aluminum.

Intensity filter 630 is configured to provide additional X-ray filtering, and is typically a uniform plate of X-ray absorbing material, such as titanium. In some embodiments, intensity filter 630 is physically coupled to or mounted on second combined filter-collimator assembly 240, and therefore is moved together with second combined filter-collimator assembly 240 by positioning mechanism 220. Alternatively, intensity filter 630 can be moved into position in X-ray path 202 separately from second combined filter-collimator assembly 240. Similarly, in some embodiments, collimator 610 is physically coupled to or mounted on compensating filter 620, and therefore is moved together with compensating filter 620 as a single assembly by positioning mechanism 220. Alternatively, collimator 610 can be moved into position in X-ray path 202 separately from compensating filter 620 by positioning mechanism 220. Together, longitudinal collimator 410 and collimator 610 define the rectangular region of X-ray imager 150 and patient 160 that is exposed to imaging beam 126.

Figure 7:
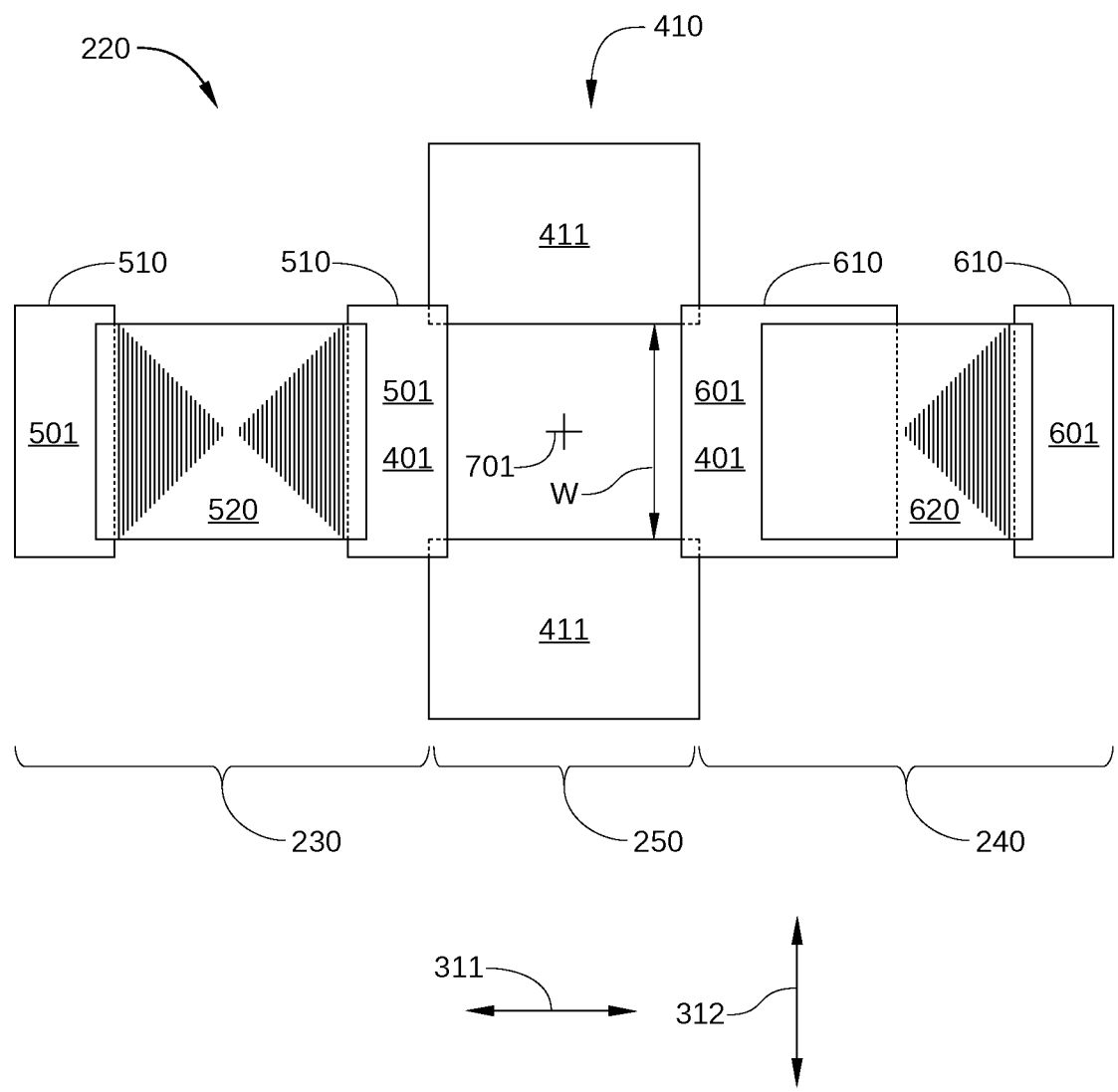
FIG. 7 is a schematic view from an X-ray imager in an RT treatment system of a positioning mechanism, a first combined filter-collimator assembly, a second combined filter-collimator assembly, and a filter-free collimator, according to an embodiment of the present disclosure.

As noted above, positioning mechanism 220 can include any suitable mechanism operable to selectively position one of first combined filter-collimator assembly 230, second combined filter-collimator assembly 240, or filter-free collimator 250 along X-ray path 202. FIG. 7 schematically illustrates one such embodiment. FIG. 7 is a schematic view from X-ray imager 150 of positioning mechanism 220, first combined filter-collimator assembly 230, second combined filter-collimator assembly 240, and filter-free collimator 250, according to an embodiment of the present disclosure. In the embodiment illustrated in FIG. 7, filter-free collimator 250 is disposed along X-ray path 202, which is substantially centered in lateral direction 311 between blades 401 of filter-free collimator 250 and in longitudinal direction 312 between blades 411 of longitudinal collimator 410. As a result, an X-ray focal point 701 of kV X-ray source 124 is located at or near a center point of the field of view defined by longitudinal collimator 410 and one of filter-free collimator 250, collimator 510, or collimator 610.

In the embodiment illustrated in FIG. 7, positioning mechanism 220 is configured as a lateral direction slider mechanism that translates first combined filter-collimator assembly 230, second combined filter-collimator assembly 240, and filter-free collimator 250 back and forth in lateral direction 311. Thus, positioning mechanism 220 selectively positions a suitable filter-collimator assembly between X-ray imager 150 and kV X-ray source 124.

In some embodiments, blades 411 of longitudinal collimator 410 are set a fixed distance W apart and are fixed in position relative to positioning mechanism 220. Alternatively, blades 411 can be movable in longitudinal direction 312 to adjust the X-ray field size and location in longitudinal direction 312. In such embodiments, blades 411 can be independently movable, thereby allowing asymmetrical field-size adjustments in longitudinal direction 312. Alternatively or additionally, blades 411 can be mechanically coupled to each other and moved in conjunction with each other in longitudinal direction 312. In some embodiments, blades 411 are fixed in position relative to kV X-ray source 124.

In some embodiments, blades 411 are mounted on positioning mechanism 220. In such an embodiment, there is generally a different pair of blades 411 for each position of positioning mechanism 220: one pair associated with first combined filter-collimator assembly 230, one pair associated with second combined filter-collimator assembly 240, and one pair associated with filter-free collimator 250. Consequently, in such embodiments, there can be a different longitudinal field size for each slider position of positioning mechanism 220.

In some embodiments, positioning mechanism 220 is moved in lateral direction 311 via a motorized actuator (not shown). Alternatively or additionally, positioning mechanism can be moved in lateral direction 311 manually, or by any other suitable actuation mechanism.

Figure 8:
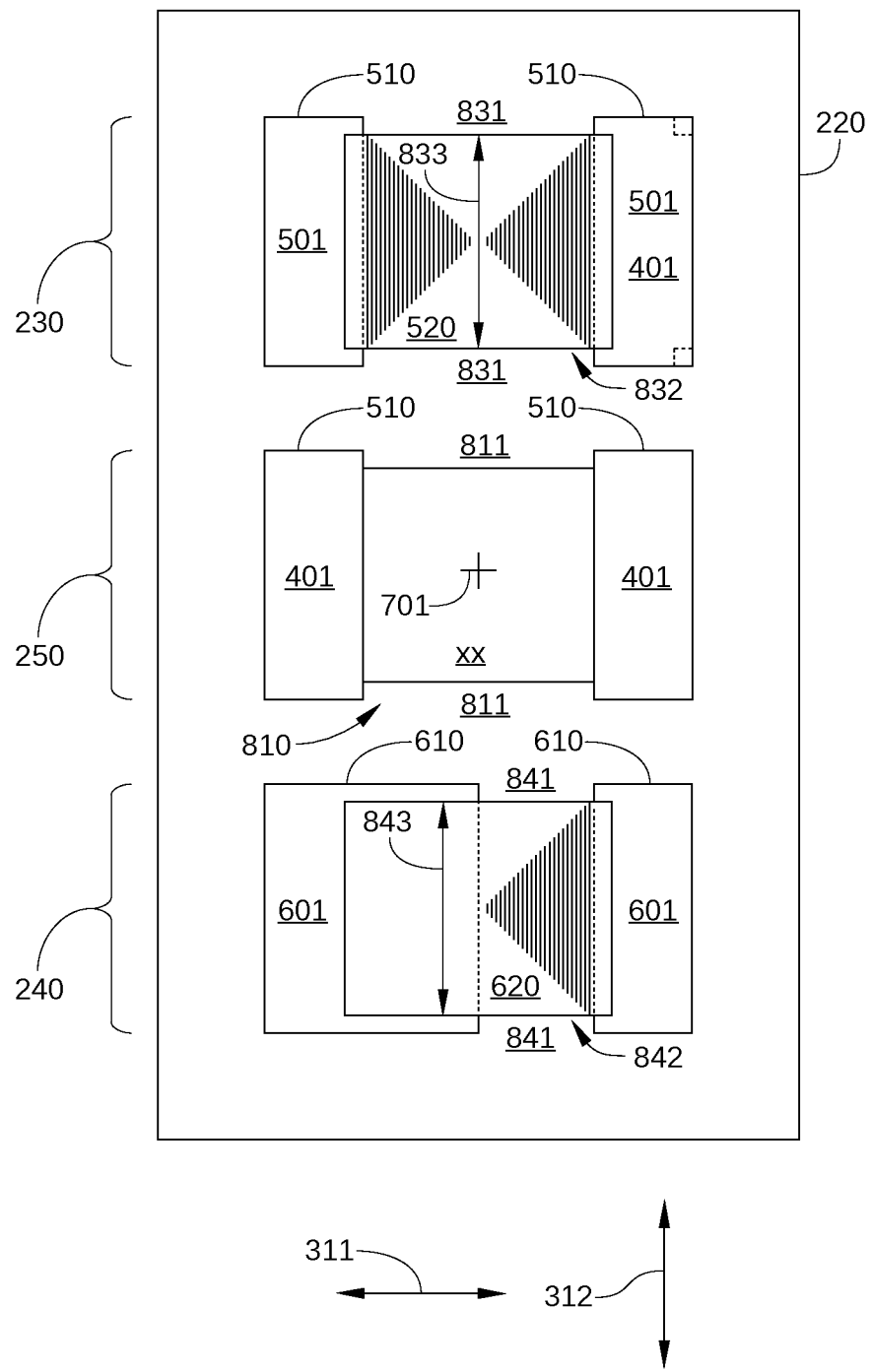
FIG. 8 is a schematic view from an X-ray imager in an RT treatment system of a positioning mechanism, a first combined filter-collimator assembly, a second combined filter-collimator assembly, and a filter-free collimator, according to an embodiment of the present disclosure.

In some embodiments, positioning mechanism 220 is configured to translate first combined filter-collimator assembly 230, second combined filter-collimator assembly 240, and filter-free collimator 250 in longitudinal direction 312 instead of in lateral direction 311. FIG. 8 schematically illustrates one such embodiment. FIG. 8 is a schematic view from X-ray imager 150 of positioning mechanism 220, first combined filter-collimator assembly 230, second combined filter-collimator assembly 240, and filter-free collimator 250, according to an embodiment of the present disclosure. In the embodiment illustrated in FIG. 8, positioning mechanism 220 translates first combined filter-collimator assembly 230, second combined filter-collimator assembly 240, and filter-free collimator 250 in longitudinal direction 312. Filter-free collimator 250 is shown disposed along X-ray path 202 (not shown). As a result, X-ray focal point 701 of kV X-ray source 124 is located at or near a center point of the field of view defined by filter-free collimator 250 and blades 811 of a longitudinal collimator 810 associated therewith.

It is noted that when positioning mechanism 220 is configured to translate longitudinally, a different longitudinal collimator is associated with each of filter-free collimator 250, first combined filter-collimator assembly 230, second combined filter-collimator assembly 240. For example, in the embodiment illustrated in FIG. 8, longitudinal collimator plates 831 form the top and bottom edges of an opening 832 and perform the function of blades 411 in FIG. 4 for first combined filter-collimator assembly 230. Thus, longitudinal collimator plates 831 define the longitudinal dimension 833 of first combined filter-collimator assembly 230. Similarly, longitudinal collimator plates 841 form the top and bottom edges of an opening 842 and perform the function of blades 411 in FIG. 4 for second combined filter-collimator assembly 240. Thus, longitudinal collimator plates 841 define the longitudinal dimension 843 of second combined filter-collimator assembly 240.

It is further noted that positioning mechanism 220 is generally larger in embodiments in which translation of combined filter-collimator assemblies is in longitudinal direction 312. However, advantageously, in such embodiments, positioning accuracy of the longitudinal sliding motion has less impact on performance of the imaging system when moving the slider longitudinally.

In other embodiments, positioning mechanism 220 can be configured to selectively rotate one of first combined filter-collimator assembly 230, second combined filter-collimator assembly 240, or filter-free collimator 250 into X-ray path 202. For example, in one such embodiment, each of first combined filter-collimator assembly 230, second combined filter-collimator assembly 240, and filter-free collimator 250 are disposed in a planar array that is rotated by positioning mechanism 220 in a plane parallel to X-ray imager 150.

Figure 9:
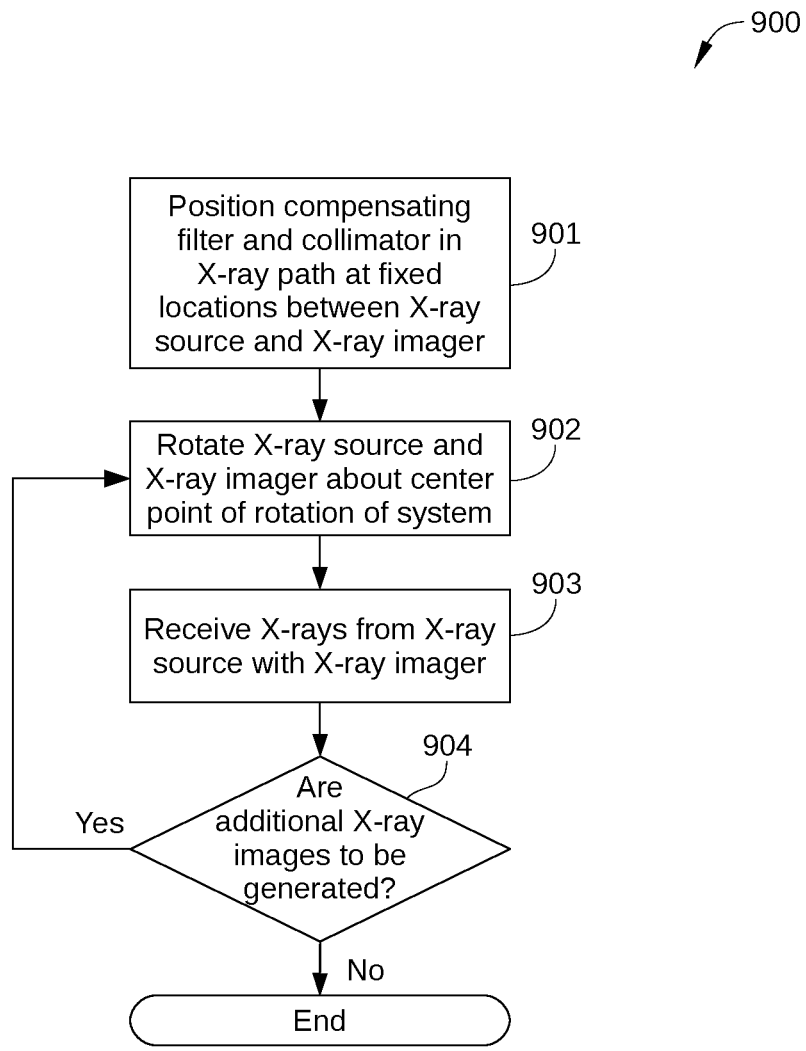
FIG. 9 sets forth a flowchart summarizing an example method for generating an X-ray image, according to one or more embodiments of the present disclosure.

FIG. 9 sets forth a flowchart summarizing an example method for generating an X-ray image, according to one or more embodiments of the present disclosure. The method may include one or more operations, functions, or actions as illustrated by one or more of blocks 901-904. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with RT treatment system 110 of FIGS. 1-8, persons skilled in the art will understand that any suitably configured system is within the scope of the present disclosure.

In the embodiment described in conjunction with FIG. 9, the control algorithms for the method steps reside in and/or are performed by image acquisition and treatment control computer 131. In other embodiments, such control algorithms may reside in and/or be performed by any other suitable control circuit or computing device.

A method 900 begins at step 901, in which a first collimator (for example, collimator 510) is positioned in X-ray path 202 at distance L2 from kV X-ray source 124, and a first compensating filter (for example, compensating filter 520) is positioned in X-ray path 202 at distance L4 from kV X-ray source 124. The first collimator is configured with a first opening (for example, opening 502), so that when the first collimator is positioned at distance L2 from X-ray imager 150, the first opening defines a width of a first imaging field, such as the width of a patient head 302 on couch 123 or half the width of a patient thorax 301. In addition, the first collimator is positioned a fixed distance L2-L4 from in X-ray path 202 from the first compensating filter. When positioned at the fixed distance L2-L4 in X-ray path 202 from the first collimator, the first compensating filter is located so that a photon flux of X-rays from kV X-ray source 124 on X-ray imager 150 is more balanced than when the first compensating filter is not positioned in the first imaging field at the distance L2-L4 from the first collimator.

In some embodiments, the first collimator and the first compensating filter are positioned in step 901 via a single mechanical operation. The single mechanical operation generally includes one of a lateral sliding motion, a longitudinal sliding motion, and a planar rotational motion of the first collimator and the first compensating filter. In such embodiments, a positioning mechanism can perform the single mechanical operation. In some embodiments, the lateral sliding motion, the longitudinal sliding motion, or the planar rotational motion also includes the motion of a second collimator out of X-ray path 202. In such embodiments, the lateral sliding motion, the longitudinal sliding motion, or the planar rotational motion may further include motion of a corresponding second compensation filter out of X-ray path 202. Furthermore, in such embodiments, the lateral sliding motion, the longitudinal sliding motion, or the planar rotational motion of the second collimator and/or the corresponding second compensation filter may be performed simultaneously with the lateral sliding motion, longitudinal sliding motion, or planar rotational motion of the first collimator and the first compensating filter.

In step 902, while i) X-ray imager 150 is positioned at a the fixed imaging distance along X-ray path 202 from kV X-ray source 124 of step 901, ii) the first collimator is positioned in X-ray path 202 at the first fixed distance along X-ray path 202 from kV X-ray source 124, and iii) the first compensating filter is positioned in X-ray path 202 at the second fixed distance along X-ray path 202 from the first collimator, the X-ray source and the X-ray imager are rotated about center point of rotation 201 to a certain rotational location with respect to a patient on couch 123.

In step 903, while kV X-ray source 124 and X-ray imager 150 are rotated about center point of rotation 201, X-rays generated by kV X-ray source 124 are received with X-ray imager 150, which can then generate an X-ray image.

In step 904, image acquisition and treatment control computer 131 determines whether additional X-ray images are to be generated by X-ray imager 150. If yes, method 900 proceeds back to step 902, components of RT treatment system 110 continue to rotate about patient 160, and additional X-ray images are generated; if no, method 900 terminates.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. An imaging system configured to rotate about a center point of rotation, the imaging system comprising:
    an X-ray source configured to direct X-rays along an X-ray path that passes through the center point of rotation to an X-ray imager;
    the X-ray imager, which is positioned at a fixed imaging distance along the X-ray path from the X-ray source and is configured to generate an X-ray image from the X-rays;
    a first combined filter-collimator assembly that includes a first collimator configured with a first opening and a first compensating filter, wherein the first collimator and the first compensating filter are fixed in position relative to each other and the first opening is formed by two blades that oppose each other; and
    a positioning mechanism that is configured to position the first combined filter-collimator assembly in the X-ray path so that:
        the first collimator is in the X-ray path at a first fixed distance along the X-ray path from the X-ray source and the first opening defines a width of a first imaging field; and
        the first compensating filter is in the first imaging field at a second fixed distance along the X-ray path from the first collimator.

2. The imaging system of claim 1, further comprising a second combined filter-collimator assembly that includes a second collimator configured with a second opening and wherein the positioning mechanism is further configured to:
    position the first collimator and the first compensating filter out of the X-ray path; and
    position the second collimator in the X-ray path at a third fixed distance from the X-ray source along the X-ray path so that the second opening defines a width of a second imaging field.

3. The imaging system of claim 2, wherein the positioning mechanism is configured to position the first collimator and the first compensating filter out of the X-ray path and position the second collimator in the X-ray path at the third fixed distance with a single mechanical operation.

4. The imaging system of claim 3, wherein the single mechanical operation includes a motion of the first collimator, the first compensating filter, and the second collimator in a direction perpendicular to the X-ray path.

5. The imaging system of claim 2, wherein the second combined filter-collimator assembly further includes a second compensating filter that is fixed in position relative to the second collimator and the positioning mechanism is further configured to position the second compensating filter in the second imaging field at a fourth fixed distance from the second collimator along the X-ray path.

6. The imaging system of claim 2, wherein the X-ray imager is disposed at the fixed imaging distance along the X-ray path from the X-ray source when the first collimator is positioned in the X-ray path at the first fixed distance from the X-ray source and when the second collimator is positioned in the X-ray path at the third fixed distance from the X-ray source.

7. The imaging system of claim 2, wherein the positioning mechanism is configured to simultaneously position the first combined filter-collimator assembly out of the X-ray path and position the second collimator of the second combined filter-collimator assembly in the X-ray path at the second fixed distance.

8. The imaging system of claim 1, wherein the X-ray imager is configured to:
    generate images in a first imaging position, in which a first portion of the X-ray imager is disposed at the fixed imaging distance along the X-ray path from the X-ray source; and
    generate images in a second imaging position, in which a second portion of the X-ray imager is disposed at the fixed imaging distance along the X-ray path from the X-ray source and the X-ray imager is displaced from the first imaging position in a direction perpendicular to the X-ray path.

9. The imaging system of claim 8, wherein the first portion of the X-ray imager comprises a center point of an X-ray detection surface of the X-ray imager and the second portion comprises an edge portion of the X-ray imager.

10. The imaging system of claim 1, wherein the positioning mechanism is configured to position the first compensating filter in the first imaging field at the fixed distance from the first collimator along the X-ray path and not at any other distance from the first collimator when the first compensating filter is in the first imaging field.

11. The imaging system of claim 1, further comprising a second collimator that is disposed between the X-ray source and the X-ray imager and includes a second opening that defines a length of the first imaging field.

12. The imaging system of claim 11, wherein the second collimator includes movable blades that modify the second opening.

13. The imaging system of claim 12, wherein the movable blades are configured to change a width of the second opening.

14. The imaging system of claim 12, wherein the movable blades are configured to move independently from each other.

15. The imaging system of claim 12, wherein the movable blades are configured to change a longitudinal location of the second opening.

16. A method of generating an X-ray image in a system that includes an X-ray source and an X-ray imager, wherein the X-ray source is configured to direct X-rays along an X-ray path that passes through a center point of rotation of the system to the X-ray imager and the X-ray imager is configured to generate an X-ray image from the X-rays, the method comprising:

positioning in the X-ray path a combined filter-collimator assembly that includes a first collimator configured with a first opening that is formed by two blades that oppose each and a first compensating filter, so that the first collimator is at a first fixed distance along the X-ray path from the X-ray source and defines a width of a first imaging field and the first compensating filter is at a second fixed distance along the X-ray path from the first collimator;

while the imager is positioned at a fixed imaging distance along the X-ray path from the X-ray source, the first collimator is positioned in the X-ray path at the first fixed distance along the X-ray path from the X-ray source, and the first compensating filter is positioned in the X-ray path at the second fixed distance along the X-ray path from the first collimator, rotating the X-ray source and the X-ray imager about the center point of rotation; and while rotating the X-ray source and the X-ray imager about the center point of rotation, receiving the X-rays with the X-ray imager.

17. The method of claim 16, wherein positioning the combined filter-collimator assembly so that the first collimator is in the X-ray path at the first fixed distance and the first compensating filter is in the X-ray path at the second fixed distance comprises positioning a second collimator out of the X-ray path.

18. The method of claim 16, wherein positioning the first collimator in the X-ray path, positioning the first compensating filter in the X-ray path, and positioning second collimator out of the X-ray path is performed via a single mechanical operation.

19. The method of claim 16, wherein the first collimator and the first compensating filter are fixed in position relative to each other in the combined filter-collimator assembly.

20. The method of claim 16, wherein the two blades oppose each other in a lateral direction that is perpendicular to the X-ray path and are positioned to limit an extent of exposure to the X-rays in the lateral direction to no more than the width of the X-ray imager.

\* \* \* \* \*